US008882668B2

(12) United States Patent
Thompson

(10) Patent No.: US 8,882,668 B2
(45) Date of Patent: Nov. 11, 2014

(54) METHOD AND PROCESS FOR BODY COMPOSITION MANAGEMENT

(75) Inventor: Elizabeth S. Thompson, Avon, IN (US)

(73) Assignee: Elizabeth S. Thompson ( * ) Notice: Subject to any disclaimer, the term of this patent is extended or adjusted under 35 U.S.C. 154(b) by 1214 days.

(21) Appl. No.: 11/985,993

(22) Filed: Nov. 19, 2007

(65) Prior Publication Data
US 2009/0131814 A1 May 21, 2009

(51) Int. Cl.
A61B 5/00 (2006.01)
A61B 5/083 (2006.01)

(52) U.S. Cl.
CPC ............... A61B 5/083 (2013.01); A61B 5/411 (2013.01); A61B 5/4869 (2013.01)
USPC ............................................ 600/301; 600/300

(58) Field of Classification Search
USPC ........... 600/300, 301; 128/903–905, 920, 921
See application file for complete search history.

(56) References Cited

U.S. PATENT DOCUMENTS

| | | | |
|---|---|---|---|
| 3,213,684 A | 10/1965 | Seaton et al. | |
| 3,220,255 A | 11/1965 | Scranton et al. | |
| 3,250,270 A | 5/1966 | Bloom | |
| 3,306,283 A | 2/1967 | Arp | |
| 3,799,149 A | 3/1974 | Rummel et al. | |
| 3,991,304 A | 11/1976 | Hillsman | |
| 4,051,847 A | 10/1977 | Henkin | |
| 4,078,554 A | 3/1978 | Lemaitre et al. | |
| 4,095,274 A | 6/1978 | Gordon | |
| 4,100,401 A | 7/1978 | Tutt et al. | |
| 4,151,668 A | 5/1979 | Hungerford | |
| 4,159,416 A | 6/1979 | Brejnik et al. | |
| 4,184,371 A | 1/1980 | Brachet | |
| 4,186,735 A | 2/1980 | Henneman et al. | |
| 4,188,946 A | 2/1980 | Watson et al. | |
| 4,192,000 A | 3/1980 | Lipsey | |
| 4,221,224 A | 9/1980 | Clark | |
| 4,221,959 A | 9/1980 | Sessler | |
| 4,244,020 A | 1/1981 | Ratcliff | |
| 4,321,674 A | 3/1982 | Krames et al. | |
| 4,341,867 A | 7/1982 | Johansen | |
| 4,359,057 A | 11/1982 | Manzella | |
| 4,369,652 A | 1/1983 | Gundlach | |
| 4,380,802 A | 4/1983 | Segar et al. | |
| 4,386,604 A | 6/1983 | Hershey | |
| 4,387,777 A | 6/1983 | Ash | |
| 4,406,289 A | 9/1983 | Wesseling | |
| 4,463,764 A | 8/1984 | Anderson et al. | |
| 4,539,997 A | 9/1985 | Wesseling | |
| 4,566,461 A | 1/1986 | Lubell et al. | |
| 4,571,682 A | 2/1986 | Silverman et al. | |
| 4,572,208 A | 2/1986 | Cutler et al. | |

(Continued)

OTHER PUBLICATIONS

CORELIFE. http://www.1corelife.com/ accessed Jul. 8, 2008.

Primary Examiner — William Thomson
Assistant Examiner — Bobby Soriano

(57) ABSTRACT

A weight management method and system measures and utilizes an individual's specific body composition and metabolic rates to provide a nutritional plan designed to the individual's specific weight management goals, including weight loss, weight gain or weight control. The system is composed of four primary components: 1) body composition testing; 2) metabolic rate testing; 3) Registered Dietitian counseling; and 4) message therapy. These components are utilized to provide a system that utilizes behavior modification and stress management to allow the individual to meet his or her weight management goals through a healthy, stable process.

17 Claims, 8 Drawing Sheets

(56) References Cited

U.S. PATENT DOCUMENTS

| | | | |
|---|---|---|---|
| 4,575,804 | A | 3/1986 | Ratcliff |
| 4,629,015 | A | 12/1986 | Fried et al. |
| 4,640,130 | A | 2/1987 | Sheng |
| 4,650,218 | A | 3/1987 | Hawke |
| 4,676,253 | A | 6/1987 | Newman |
| 4,709,331 | A | 11/1987 | Barkett et al. |
| 4,731,726 | A | 3/1988 | Allen, III |
| 4,753,245 | A | 6/1988 | Gedeon |
| 4,757,453 | A | 7/1988 | Nasiff |
| 4,796,182 | A | 1/1989 | Duboff |
| 4,796,639 | A | 1/1989 | Snow et al. |
| 4,803,625 | A | 2/1989 | Fu et al. |
| 4,807,169 | A | 2/1989 | Overbeck |
| 4,823,808 | A | 4/1989 | Clegg et al. |
| 4,841,982 | A | 6/1989 | Nikiforov |
| 4,853,854 | A | 8/1989 | Behar et al. |
| 4,855,945 | A | 8/1989 | Sakai |
| 4,856,531 | A | 8/1989 | Merilainen |
| 4,888,718 | A | 12/1989 | Furuse |
| 4,891,756 | A | 1/1990 | Williams, III |
| 4,894,793 | A | 1/1990 | Ikemoto et al. |
| 4,909,259 | A | 3/1990 | Tehrani |
| 4,911,256 | A | 3/1990 | Attikiouzel |
| 4,951,197 | A | 8/1990 | Mellinger |
| 4,954,954 | A | 9/1990 | Madsen et al. |
| 4,972,842 | A | 11/1990 | Korten |
| 5,033,561 | A | 7/1991 | Hettinger |
| 5,060,656 | A | 10/1991 | Howard |
| 5,105,825 | A | 4/1992 | Dempster |
| 5,117,674 | A | 6/1992 | Howard |
| 5,207,580 | A | 5/1993 | Strecher |
| 5,233,520 | A | 8/1993 | Kretsch et al. |
| 5,263,491 | A | 11/1993 | Thornton |
| 5,340,315 | A | 8/1994 | Kaye |
| 5,363,857 | A | 11/1994 | Howard |
| 5,379,777 | A | 1/1995 | Lomask |
| 5,388,043 | A | 2/1995 | Hettinger |
| 5,398,688 | A | 3/1995 | Laniado |
| 5,412,560 | A | 5/1995 | Dennison |
| 5,412,564 | A | 5/1995 | Ecer |
| 5,450,750 | A | 9/1995 | Abler |
| 5,478,989 | A | 12/1995 | Shepley |
| 5,503,151 | A | 4/1996 | Harnoncourt et al. |
| 5,620,005 | A | 4/1997 | Ganshorn |
| 5,673,691 | A | 10/1997 | Abrams |
| 5,691,927 | A | 11/1997 | Gump |
| 5,692,501 | A * | 12/1997 | Minturn .................. 600/301 |
| 5,704,350 | A | 1/1998 | Williams, III |
| 5,729,479 | A | 3/1998 | Golan |
| 5,819,735 | A | 10/1998 | Mansfield et al. |
| 5,839,901 | A | 11/1998 | Karkanen |
| 5,840,019 | A | 11/1998 | Wirebaugh |
| 5,933,136 | A | 8/1999 | Brown |
| 5,954,510 | A | 9/1999 | Merrill et al. |
| 5,954,640 | A | 9/1999 | Szabo |
| 5,967,789 | A | 10/1999 | Segel |
| 5,980,447 | A | 11/1999 | Trudeau |
| 6,032,119 | A | 2/2000 | Brown et al. |
| 6,039,688 | A | 3/2000 | Douglas |
| 6,040,531 | A | 3/2000 | Miller-Kovach et al. |
| 6,066,101 | A | 5/2000 | Johnson |
| 6,077,193 | A | 6/2000 | Buhler |
| 6,083,006 | A | 7/2000 | Coffman |
| 6,135,950 | A | 10/2000 | Adams |
| 6,306,099 | B1 | 10/2001 | Morris |
| 6,336,136 | B1 | 1/2002 | Harris |
| 6,428,320 | B1 | 8/2002 | Archuleta |
| 6,436,036 | B1 | 8/2002 | Miller-kovach |
| 6,458,080 | B1 | 10/2002 | Brown |
| 6,478,736 | B1 | 11/2002 | Mault |
| 6,482,158 | B2 | 11/2002 | Mault |
| 6,508,762 | B2 | 1/2003 | Karnieli |
| 6,513,532 | B2 | 2/2003 | Mault |
| 6,538,215 | B2 | 3/2003 | Montagnino |
| 6,607,483 | B1 | 8/2003 | Holland |
| 6,648,827 | B2 * | 11/2003 | Heikkila et al. ............. 600/502 |
| 6,663,564 | B2 | 12/2003 | Miller-kovach |
| 6,675,041 | B2 | 1/2004 | Dickinson |
| 6,699,188 | B2 | 3/2004 | Wessel |
| 6,778,926 | B2 | 8/2004 | Dempster |
| 6,790,178 | B1 | 9/2004 | Mault |
| 6,816,807 | B2 | 11/2004 | Kriger |
| 6,872,077 | B2 | 3/2005 | Yeager |
| 6,875,020 | B2 | 4/2005 | Niddrie |
| 6,878,885 | B2 | 4/2005 | Miller-kovach |
| 6,910,373 | B2 * | 6/2005 | Dempster et al. ............. 73/149 |
| 6,980,999 | B1 | 12/2005 | Grana |
| 7,024,369 | B1 | 4/2006 | Brown |
| 7,063,665 | B2 | 6/2006 | Hasegawa |
| 7,090,638 | B2 | 8/2006 | Vidgen |
| 7,175,595 | B1 | 2/2007 | Stegmann |
| 7,204,145 | B2 | 4/2007 | Heink |
| 7,238,156 | B1 | 7/2007 | Adamczyk |
| 7,247,023 | B2 | 7/2007 | Peplinski |
| 7,261,690 | B2 | 8/2007 | Teller |
| 7,361,143 | B2 | 4/2008 | Kirchhoff |
| 2002/0107433 | A1 * | 8/2002 | Mault .................. 600/300 |
| 2003/0186202 | A1 * | 10/2003 | Isenberg .................. 434/236 |
| 2004/0102684 | A1 * | 5/2004 | Kawanishi et al. ......... 600/300 |
| 2007/0060803 | A1 * | 3/2007 | Liljeryd et al. ............ 600/301 |
| 2007/0238593 | A1 * | 10/2007 | Ellis et al. ................. 482/148 |
| 2008/0058610 | A1 * | 3/2008 | Sato et al. ................. 600/300 |
| 2008/0183398 | A1 * | 7/2008 | Petrucelli ................... 702/19 |

* cited by examiner

FIGURE 1

| Week | Plan |
|---|---|
| 1 | Metabolic Testing and Body Composition Testing |
| 2 | Consultation with Registered Dietitian |
| 3 | Body Composition Testing |
| 4 | Massage Therapy Reward |
| 5 | Body Composition Testing |
| 6 | Massage Therapy Reward |
| 7 | Body Composition Testing |
| 8 | Massage Therapy Reward |
| 9 | Body Composition Testing |
| 10 | Massage Therapy Reward |
| 11 | Body Composition Testing |
| 12 | Massage Therapy Reward |
| 13 | Body Composition Testing |
| 14 | Massage Therapy Reward |
| 15 | Body Composition Testing |
| 16 | Massage Therapy Reward |
| 17 | Body Composition Testing |
| 18 | Massage Therapy Reward |
| 19 | Body Composition Testing |
| 20 | Massage Therapy Reward |
| 21 | Body Composition Testing |
| 22 | Massage Therapy Reward |
| 23 | Body Composition Testing |
| 24 | Massage Therapy Reward |
| 25 | Metabolic Testing and Body Composition Testing |
| 26 | Consultation with Registered Dietician and Massage Therapy Reward |

FIGURE 2

| Name | Mr. X |
|---|---|
| Member # | 1010 |
| Date: Visit 1 | 29-Oct-07 |
| DOB | 10/10/1978 |
| Height | 6'2" |

| Body Fat Rating | Male | Female |
|---|---|---|
| Risky (Too High) | >30% | >40% |
| Excess Fat | 21-30% | 31-40% |
| Moderately Lean | 13-20% | 23-30% |
| Lean | 9-12% | 19-22% |
| Ultra Lean | 5-8% | 15-18% |
| Risky (Too Low) | <5% | <15% |

ClubMET Progress Report

| Visit | Date | BodPod Weight | BodPod Lean Mass | BodPod Fatty Tissue | BodPod Percent Body Fat | Notes | Reward Earned | Date Reward Applied |
|---|---|---|---|---|---|---|---|---|
| 1 | 29-Oct-07 | 339.2 | 166.9 | 172.3 | 50.7% | RMR 2563   Danger 2051   Target 2307 | | |
| 2 | 30-Oct-07 | | | | | | 30 | |
| 3 | 7-Nov-07 | 339.6 | 168.2 | 171.4 | 50.4% | | | 30 RD/M |
| 4 | 21-Nov-07 | | | | | | 30 | |
| 5 | 21-Nov-07 | 335.7 | 167.7 | 168.0 | 50.0% | | | 30 RD/M |
| 6 | 28-Nov-07 | | | | | | 30 | |
| 7 | 5-Dec-07 | 331.8 | 167.4 | 164.4 | 49.5% | | | 30 RD/M |
| 8 | 11-Dec-07 | | | | | | 30 | |
| 9 | 19-Dec-07 | 331.8 | 169.6 | 162.2 | 48.9% | | | 30 RD/M |
| 10 | 31-Dec-07 | | | | | | 30 | |
| 11 | 2-Jan-08 | 328.6 | 171.8 | 156.8 | 47.7% | | | 30 RD/M |
| 12 | 7-Jan-08 | | | | | | 30 | |
| 13 | 15-Jan-08 | 327.7 | 168.2 | 159.5 | 48.6% | RMR 2578   Danger 2064   Target 2320 | | 0 RD/M |
| 14 | 16-Jan-08 | | | | | RD Counseling | 0 | |
| 15 | 30-Jan-08 | 321.4 | 168.3 | 153.1 | 47.6% | | | 30 RD/M |
| 16 | 5-Feb-08 | | | | | | 30 | |
| 17 | 14-Feb-08 | 319.4 | 166.1 | 153.3 | 48.0% | | | 0 RD/M |
| 18 | N/A | | | | | | 0 | |
| 19 | 28-Feb-08 | 316.5 | 166.9 | 149.6 | 47.2% | | | 30 RD/M |
| 20 | 2-Mar-08 | | | | | | 30 | |
| 21 | 11-Mar-08 | 311.8 | 165.8 | 146.0 | 46.8% | | | 30 RD/M |
| 22 | 18-Mar-08 | | | | | | 30 | |
| 23 | 25-Mar-08 | 308.0 | 166.0 | 142.0 | 46.1% | | | 30 RD/M |
| 24 | | | | | | | | RD/M |
| 25 | 6-Apr-08 | 313.9 | 171.1 | 142.8 | 45.4% | RMR   Danger   Target | 0 | RD/M |
| 26 | | | | | | | | RD/M |
| | TOTAL | -25.3 | +4.2 | -29.5 | -5.30% | | | |

FIGURE 3

Resting Metabolic Rate

The results of your Resting Metabolic Rate test show precisely how many calories YOUR body burns each day. Results are considered accurate for 12 weeks. According to your metabolism, we have defined specific Target Calories to meet each day in order to achieve your goal.

Date:                              September 15, 2007
Recommended Return Date:           December 7, 2007
Name:
Gender:                            Male
Age:                               27
Height:                            6ft 2in
Weight:                            327.7 lbs
Technician:
Test ID:                           106C

What You Burn

Resting Metabolic Rate (RMR)       2578 Calories/Day[1]
Normal Daily Activity              771 Calories/Day[2]
Daily Expenditure                  3349 Calories/Day[3]

[1] Metabolic Measurement performed today
[2] Normal lifetime activities throughout the day
[3] RMR + Normal Daily Activity

*Additional Exercise                268 Calories/half-hour

NOTE: Exercise is estimated based on your RMR measurement. It considers ½ hour of moderate exercise. This system defines moderate exercise as ½ hour of cardiovascular exercise maintaining a heart rate equal to 0.7 x (220 − your age).

FIGURE 4

Body Composition Test Results

| | |
|---|---|
| Percent Body Fat | 48.6 % |
| Body Fat (Measured in Pounds) | 159.5 Pounds |
| | |
| Percent Lean Body Mass | 51.4 % |
| Lean Body Mass (Measured in Pounds) | 168.2 Pounds |
| TOTAL WEIGHT: | 327.7 |

| * | Body Fat Rating | Male | Female | Explanation |
|---|---|---|---|---|
| | Risky (Too High) | >30% | >40% | This body composition poses serious health risks. |
| | Excess Fat | 21-30% | 31-40% | Indicates an excess accumulation of fat over time. |
| | Moderately Lean | 13-20% | 23-30% | Fat level is acceptable for good health. |
| | Lean | 9-12% | 19-22% | Lower body fat levels than many people. This range is excellent for health and longevity. |
| | Ultra Lean | 5-8% | 15-18% | Fat levels sometimes found in elite athletes. |
| | Risky (Too Low) | <5% | <15% | Too little body fat can present health risks, especially for women. |

*\* As stated by the American College of Sports Medicine*

FIGURE 5

Health Questionnaire -- General Information

Name_____ DOB__/__/__ Date_____
Address_____City_____State____Zip_____
Phone_____ Email_____
Were you referred to us? Y N  If yes, by whom?_____
If the person that referred you is a health/fitness professional, what organization are they with?
_____

If you were not referred to us, how did you hear about us?_____
Name of your Physician_____
Name of Practice _____ City of Practice _____
May we send progress reports to your physician? _____
Person to call in an emergency_____Phone_____

To what do you attribute your current weight gain/loss?
_____
_____

What made you take the step to commit to your body?
_____
_____

Do you have a special event coming up that you would like to be prepared for? Y N
If yes, what is the event?_____
If yes, when is the event? _____
Has a medical professional advised you to lose weight to improve your health? Y N
If yes, what is his/her name? _____
Organization _____Phone_____
What else would you like to tell us?
_____
_____
_____

FIGURE 6

Health Questionnaire -- Food Preferences and Habits

Make a list of your favorite foods.

_____     _____
_____     _____
_____     _____
_____     _____

Make a list of foods that you dislike.

_____     _____
_____     _____
_____     _____
_____     _____

Are you allergic to any types or kinds of foods?
_____
_____

HABITS
What time do you normally wake up?           _____
What time do you normally go to bed at night?  _____
If you smoke, how many per day?              _____
If you smoke, how many years have you smoked?  _____
If you drink alcoholic beverages, what and how many per day?_____
How many meals per day do you eat? _____
How many snacks per day do you have? _____
Do you eat breakfast? _____
Describe your average caffeine intake: _____
Do you often eat late at night? _____
Are you a "stress-eater"? _____
Are you a "stress non-eater?" _____

Have you tried any other programs or methods to attain your goals? Please explain:
_____
_____
_____
_____

What were your results?
_____
_____

Have you ever had your body fat tested?  ☐ Yes  ☐ No
If yes, how was it tested and when?
_____

FIGURE 7

Please list below everything you have eaten in one 24 hour period. Be sure to include snacks and beverages, including water. Please be very specific regarding types of foods (2% milk, fat-free cheese, low-sodium soup etc.). The more accurate you are, the more accurate your results will be.

| FOOD and INGREDIENTS | PREPARATION (baked, fried, etc) | AMOUNT (cups, oz, each, etc.) | TIME | LOCATION |
|---|---|---|---|---|
| Example: Chicken Breast | Grilled | 5 oz. | 12:00 pm | Work |
| Example: Tossed Salad with lettuce, tomatoes, cucumbers, and carrots | Chopped | 2 cups | 5:00 pm | Home |
| | | | | |
| | | | | |
| | | | | |
| | | | | |
| | | | | |
| | | | | |
| | | | | |
| | | | | |
| | | | | |
| | | | | |
| | | | | |
| | | | | |

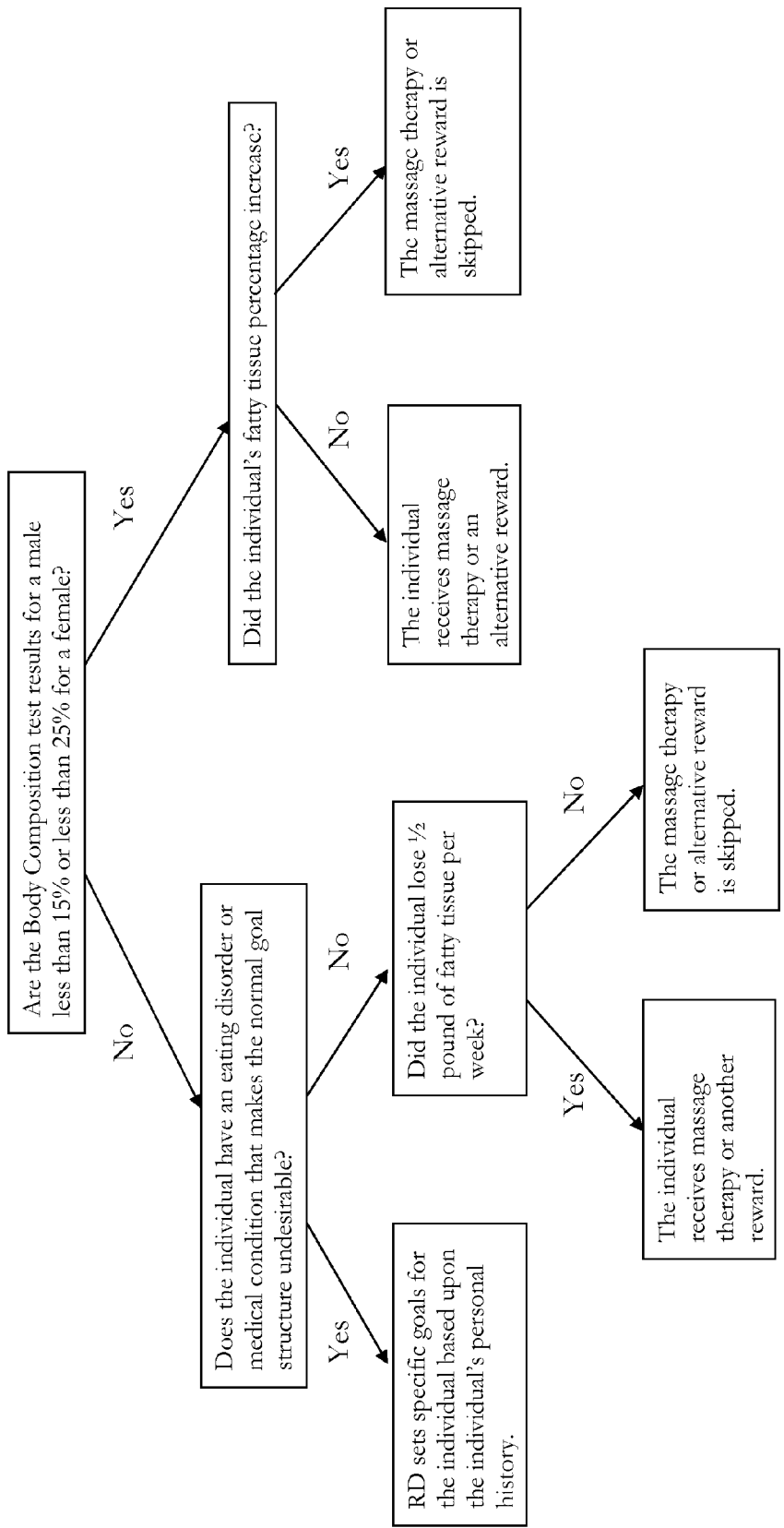

METHOD AND PROCESS FOR BODY COMPOSITION MANAGEMENT

FIELD OF THE INVENTION

The present invention relates generally to a method for weight management and control, and more particularly to a method for tailoring a weight management program to the specific needs of an individual utilizing the individual's body composition and metabolic rate in combination with nutrition counseling and massage therapy.

BACKGROUND OF THE INVENTION

Proper weight management is important to facilitate a healthy lifestyle and reduces the risk of major chronic diseases. The rate of obesity in the United States is nearly one-third of all adults and more than two-thirds of adults are considered overweight. The Centers for Disease Control and Prevention (CDC) has now declared obesity an epidemic. According to the U.S. Department of Agriculture's "Dietary Guidelines for Americans 2005" the high prevalence of overweight and obese adults is a great public health concern "because excess body fat leads to a higher risk for premature death, type 2 diabetes, hypertension, dyslipidemia, cardiovascular disease, stroke, gall bladder disease, respiratory dysfunction, gout, osteoarthritis, and certain kinds of cancers." The ideal for adults is to achieve and maintain a body weight that optimizes their health.

Approaches to weight and health management are numerous. Products and systems on the market include calorie counting programs, appetite suppressants, meal replacement products, prescription drugs, commercial weight loss programs and many others. The effectiveness of these products and programs vary, often because the various products are not customized to the individual.

National weight management systems such as Weight Watchers® and Jenny Craig® are based on averages. Although these programs are generally considered an improvement over merely "counting calories" the programs are still based upon averages and therefore, do not fully address each individual's variations from the average. Since these programs do not account for individual differences, the results are often less than optimal, unless the individual is average in all relevant aspects.

Another concern in the art is that many weight management systems use a simple scale to measure progress in a weight loss program. Typically, however, dieters seeking to lose weight are most interested in losing body fat. In this situation, using a scale to measure progress can be very misleading, as body weight does not necessarily reflect fat loss or gain. For instance, loss of weight may be a result of less food in the stomach, less water retention or the loss of muscle mass. Therefore, loss of body weight does not necessarily indicate loss of fat.

To more accurately determine fat loss or muscle gain, an accurate measure of body composition is required. Measuring body composition provides a more precise measure of the individual's body fat and lean tissue. Excess body fat leads to increased risk of chronic disease, while increased lean body mass, which is primarily muscle, will increase the metabolic rate in the body. Regular and accurate measuring of body composition provides important feedback necessary to optimize and allow an individual to meet their weight management goals. According to former Surgeon General, C. Everett Koop, "[b]ody fat percentage will become a new standard for health in adults."

There are many ways to measure body composition. Some methods, such as bioelectrical impedance (using the resistance of electrical flow through the body) and skinfold calipers (measuring the thickness of subcutaneous fat in multiple places on the body, such as the abdomen, arms, thighs and buttocks), have reported error rates of up to 8%. For an individual with a body fat level of 20%, an inaccurate method could indicate body fat as low as 12% or as high as 28%. Therefore, these methods can provide inaccurate and misleading information. Although no body composition measurement method currently offers 100% accuracy, some systems provide accuracy within 1 to 2%. Some of the more precise means for measuring body composition include: plethysmographic air chamber such as the BodPod Body Composition Tracking System (BodPod); Dual X-ray Absorptionmetry (DXA), magnetic resonance imaging (MRI) and computed tomography (CT). By accurately measuring body composition the individual can determine the amount of fat and lean tissue that makes up their weight, enabling more precise decisions regarding nutrition and exercise so that the individual's weight and health can best be managed and controlled.

As an individual's body composition changes, their metabolism also changes. An individual's metabolism is the process by which their body converts food into heat or energy. The rate and efficiency at which the body converts food to energy is referred to as the individual's metabolic rate. Many factors may affect an individual's metabolic rate, including genetics, eating habits and fitness level. The individual's metabolic rate is important to weight management as it allows the individual to determine how many calories that individual's body is using. A system that causes an individual to consume an extra 500 calories per day leads to one pound of weight gain per week. Conversely, eating too few calories slows down the body's metabolic rate, causing the body to store more fat and use the muscles for energy. Since many of the national programs are based on averages, individuals may be consuming too many or too few calories without knowing that the program is not right for their body.

An individual's metabolic rate can be measured by gas analysis through either direct or indirect calorimetry. A rough estimate can be determined through an equation using age, sex, height, and weight. Most national weight management programs rely on a predictive equation to estimate metabolic rate. These national programs do not address each individual's calorie-requirements through the more accurate testing of their resting metabolism rate (RMR).

A recent Journal of the American Dietetic Association (ADA) study showed that seven predictive equations, including the Harris-Benedict and the Mifflin equations do not accurately and reliably predict energy needs. Since the predictive equations only estimate RMR based upon an average person, the result of the equation is often not reliable and may differ vastly from the individual's actual RMR. Therefore, programs that utilize these equations may result in the individual consuming too many or too few calories, leading to ineffective weight control.

Accordingly, a system is needed that utilizes accurate testing of each individual's metabolic rate to calculate caloric needs. This problem has been recognized in other patents, for example, U.S. Pat. No. 6,478,736 to Mault, incorporated herein by reference, for an integrated calorie management system.

Registered Dietitians ("RD"), food and nutrition experts who hold specific certifications as required by the American Dietetic Association, have used the testing of body composition and metabolic rate for determining caloric intake needs in such settings as hospitals and universities. In most cases, individuals are referred by a physician or health professional to gain access to a Registered Dietitian. Registered Dietitians are able to utilize an individual's body composition and metabolic rate to determine the daily caloric intake necessary for the individual. These tools allow that Dietician to create a specific dietary plan for the individual based upon that individual's unique genetic and physical qualities.

Finally, massage therapy has been used as a health care practice for more than 4,000 years. Generally, massage therapy is used to improve the circulation of blood through the body to improve the healing of body tissue. Further, massage therapy is used to relieve muscle tension, increase flexibility, decrease muscular stress and relieve tension-related conditions.

Accordingly, it is the object of the present invention to provide a weight management system that accommodates the individual differences in body composition, metabolic rates and the corresponding changes therein over time into a program that facilitates proper weight management for an individual.

It is a further object of the present invention to provide a structured system wherein the individual is regularly tested so that their dietary needs may be periodically adjusted.

Yet another object of the present invention is to provide a weight management system that includes an accountability system, reinforcing behavior conducive to effective weight management and to prevent crash dieting.

It is a further object of the present invention to provide a coping mechanism for dealing with stress relating to weight management to facilitate optimal weight management.

It is another object of the present invention to encourage and teach healthy habits through access to a Registered Dietician or nutritionist in combination with testing of the individual's body composition and metabolic rates over time.

BRIEF DESCRIPTION OF THE DRAWINGS

FIG. 1 is a table showing an embodiment of the system where testing, evaluation and counseling is provided over a 26 week period.

FIG. 2 shows a progress report that is updated after each body composition testing.

FIG. 3 shows a metabolic rate testing report given to the participant after a metabolic rate test.

FIG. 4 shows a body composition chart outlining acceptable body fat levels.

FIG. 5 shows general information collected in a health questionnaire.

FIG. 6 shows health questionnaire information collected regarding the participant's food preferences and habits.

FIG. 7 shows a form used to journal food consumption over a twenty-four hour period.

FIG. 8 shows a flow chart of a goal structure for an individual who desires to lose weight.

SUMMARY OF THE INVENTION

The present invention includes processes for losing, gaining or maintaining body weight. The system includes the use of a combination of components allowing an individual to accomplish weight management goals based upon the individual's unique physiological make up.

In the preferred embodiment an individual's metabolism and body composition are tested to allow a Registered Dietitian to formulate a dietary plan based upon the testing results and the individual's medical history and weight management goals. A Bod Pod® is used to calculate the individual's body composition at predetermined intervals to measure the results of the individual's fatty tissue loss and lean mass tissue gain or maintenance. Finally, a reward formula is used to provide massage therapy for behavior modification to teach healthy weight management and to act as a coping mechanism for the stress associated with dietary changes.

DETAILED DESCRIPTION OF THE INVENTION

In accordance with the preferred embodiments of the present invention a weight management method and system is described below. After collecting personal medical information and weight management goals, the system measures and utilizes the individual's specific body composition and metabolic rates to provide a nutritional plan based upon the individual's physiological make-up. The individual's specific attributes are measured and utilized to more effectively meet the individual's weight management goals, including weight loss, weight gain or weight control. The system is designed to allow the individual to avoid or overcome many of the pitfalls that cause other weight management programs to fail.

The preferred embodiment of the present invention is composed of four primary components: 1) body composition testing; 2) metabolic rate testing; 3) Registered Dietitian counseling; and 4) massage therapy or some other goal/reward/stress management device. These components are combined within a program that utilizes behavior modification and stress management so that the individual is able to set and achieve weight management goals in a dramatically improved way.

FIG. 1 shows a table of a six month program incorporating each of the four major components into a weight management program. The program is divided into 26 weekly events (which can be shortened to 24 weeks by collapsing weeks one and two and twenty-five and twenty-six) wherein at least one of the four components is used on a weekly basis to optimize the individual's weight management goals. The program begins with both metabolic testing and body composition testing. These test results are used by a Registered Dietitian to complete a specific dietary plan based upon the individual's unique data. Throughout the 26 week program, the individual's body composition is tested every other week. Based on a formula designed to encourage healthy weight management, the body composition testing is used to determine whether the individual receives a predetermined reward, such as massage therapy.

The six month duration of the program can be longer or shorter depending upon the individual's goals. However, the six month program provides a preferred time period promoting solid, steady progress resulting in the loss of fatty tissue and not lean body mass. The six month time period also promotes a true lifestyle change. During this time, it is likely that the individual will hit a "life hurdle," i.e. vacation, job-change, move, etc . . . that may cause the individual to fail to meet their weight management goals. However, this program uses accountability, support and behavior modification to help the individual persevere through the "life hurdles" to achieve a true lifestyle change (as opposed to a quick-fix, crash-diet that often results in a high fluctuation in weight where the individual's weight bounces back worse than before, often damaging the individual's metabolism during the process).

The weekly events or visits provide accountability without requiring a large amount of the individual's time. The weekly visits allow the individual to be held accountable and receive weekly support. More frequent visits could be scheduled for individuals with fewer time constraints and commitments. Finally, weekly visits minimize the monthly costs associated with the program.

To begin the weight management program, the individual completes a health questionnaire that includes his or her medical history, current medications and health related goals. As shown in FIGS. 5-7, the questionnaire includes information on the participant's gender, height, weight, current exercise habits, weight management goals and history, factors affecting weight, factors motivating the desire to enter a weight management program (including special events and recommendations by a doctor), information relating to daily activity levels, body type, health and medical conditions. The questionnaire also asks the participant to list his or her favorite foods, foods that are disliked and known allergies to foods. The questionnaire seeks information relating to the participant's habits, prior use of other weight programs or products and a section requesting information on the participant's willingness to commit to the program. Finally, the questionnaire requires the individual to journal all food and beverages consumed over one twenty-four hour period.

In addition to collecting this information, the individual's metabolic rate and body composition is tested. This information is collected for use by a Registered Dietitian to formulate a dietary plan according to the individual's goals, metabolism, body composition and medical history.

FIG. 3 shows a metabolic rate testing report that is provided to the individual after each metabolic rate test. In the preferred embodiment, the individual's metabolic rate is tested three times over the 26 week period. Typically the individual's metabolic rate is tested at the beginning, middle and end of the program. Although, three measurements of the metabolic rate are scheduled, additional tests of the metabolic rate are made if: 1) the individual's fatty tissue loss plateaus; 2) the individual shows consistent and marked decrease in lean body mass (i.e. greater than 25% decrease in lean body mass between first body composition test and most recent body composition test); 3) there is a medical diagnosis such as hypothyroidism, diabetes, etc . . . ; or 4) there are changes in the individual's medications. Any one of the above four conditions will result in the individual's metabolic rate being re-tested, despite the test not being originally scheduled within the program. Every time the individual has his or her metabolism tested, a follow-up appointment with the RD is also scheduled to allow the participant to receive and discuss the results. If there are new recommended calorie levels or other dietary recommendations the participant also receives these changes from the RD.

The preferred method for testing the metabolic rate for this system is through indirect calorimetry, utilizing the Korr Reevue method. Indirect calorimetry measures the amount of oxygen consumed which is directly proportional to the rate of calorie expenditure. The Korr Reevue method is FDA approved, highly accurate and easy to administer. As one of ordinary skill in the art will recognize, other methods for testing metabolic rate may also be used. In choosing a testing method, important factors such as the accuracy and efficiency of the method and whether the method accounts for hormones and medications should be considered.

As seen in FIG. 1, the body composition of the individual is also tested at the beginning of the program. An individual's body composition includes the individual's percentage of body fat and the percentage of lean body mass. As shown in FIG. 4, both too high body fat and too low body fat are dangerous to the individual's health. It is desirable for men to have a body fat composition between 5 and 20 percent and for women to have a body fat composition between 15 and 30 percent.

Body composition testing shows the amount of fat pounds gained or lost. It also shows whether muscle mass is being used by the body for fuel, thereby reducing the individual's metabolism. Body composition may be calculated many different ways. The preferred embodiment utilizes a plethysmographic air chamber such as the BodPod® for testing of body composition. The BodPod is used for body composition analysis because of its accuracy of only a 1 or 2% margin of error. This device calculates body composition based upon air displacement and is easy to administer. Other methods may also be used such as DXA, MRI, or CT. Whichever method is chosen, it is beneficial to consider such factors as the accuracy of the device, the ease of testing and the cost of testing.

The preferred embodiment of the invention utilizes body composition testing every other week. However, the testing can be more or less frequent. In another embodiment of the invention, the body composition testing is done on a weekly basis for those individuals seeking more accountability and desiring a closer monitor on their body changes throughout the program. Regardless of the frequency of testing, after each body composition test, the individual is given a report as shown in FIG. 2, displaying the individual's progress throughout the program.

The system includes the use of a Registered Dietitian (RD) or nutritional counselor. The RD uses the individual's results from the metabolic testing and the body composition testing to determine appropriate dietary recommendations to help the individual achieve their weight management goals. The RD has scheduled visits with the individual, but the program also provides open access to the RD, allowing the individual to contact the RD via email, phone, internet forums, etc . . . This open access to the RD ensures that the individual is receiving accurate health management information and sufficient guidance throughout the program.

One of ordinary skill in the art will recognize that the program may also work through the utilization of another qualified counselor, for example a nutritionist or a health professional trained to utilize the body composition and metabolism results to develop a desirable dietary plan. Alternatively, an RD could also manage a group of nutritionists to implement the program. Finally, this program could be implemented through a computer program that provides calculations based upon formulas utilizing the individual's test results.

The RD develops the individual's custom dietary plan. The RD analyzes the individual's metabolic testing results, body composition testing results, medical history and stated health goals. The RD utilizes this information to formulate a specific dietary plan for the individual, designed according to their unique personal history and test results. As the RD counsels the individual, the RD provides a "danger zone" which is the number of calories that the individual should never fall below so that their metabolism is not damaged. If the individual consumes fewer than the "danger zone" caloric level then the participant's lean body mass will decrease. The RD also provides the individual with their "target calories" which is the number of calories the individual needs to eat every day in order to reach their stated goal. This caloric level is assigned by the RD and is dependent on the individual's metabolic rate and personal history.

The RD assists the individual throughout the program by answering questions, offering encouragement, analyzing and trending body composition test results, recognizing when it is time to retest metabolism and meeting with the participant in private sessions. The RD provides the participant with the number of calories that the participant needs to run itself at rest for 24-hours, for example, the calories burned through breathing, the digestive processes, etc. (resting metabolism rate RMR). The RD also provides the participant with the number of calories that the individual will burn per ½ hour of moderate exercise. Finally, the RD provides counseling and education to the participants on fitness and exercise.

In the preferred embodiment the RD utilizes a reward and behavior modification formula that can be adjusted or customized depending upon the background and the goals of the individual. The formula is used to determine whether the individual earns a bi-weekly 30 minute massage. The formula is designed to encourage proper, healthy weight loss, weight gain or weight management. It is generally accepted that the recommended rate for Total Weight Loss (fatty tissue and lean body mass) in the health and fitness industry is ½ lb to 2 lbs per week. In accordance with this general standard, the preferred embodiment of the system has a goal of ½ pound of fatty tissue loss per week to provide the participant with an attainable goal so that the participant has the opportunity to receive a massage therapy session to promote healthy stress management and behavior modification. The promise of a massage motivates the participant to make wiser choices by rewarding the participant for performance throughout their weight loss journey.

Furthermore, stress is often a major factor causing individuals to quit their attempt at weight loss. It is common for the individual to turn towards or away from food to manage stress—both of which can be detrimental to their weight management. By providing a weekly or bi-weekly massage the program replaces an old habit with a new habit as a tool for managing the stress and desire to turn to food. Accordingly, the system helps the individual attain successful, healthy weight management through behavior modification.

As most Americans are overweight or obese, the goal for a majority of the individuals is to lose weight. The program utilizes the formula as shown in FIG. 8 for weight loss: the individual must lose ½ pound of fatty tissue per week which is typically one pound of fatty tissue per (the bi-weekly) body composition test. If the individual loses one pound of fatty tissue in two weeks, they receive the 30 minute massage reward.

In the preferred embodiment, the second body composition test occurs in week 3. This is generally one week after the initial consultation with the RD. Therefore, the week 3 body composition test only requires ½ lb. of fatty tissue loss, to receive the 30 minute massage reward. The following body composition tests (weeks 5, 7, 9, etc . . . ) all occur two weeks apart and therefore require 1.0 pound of fatty tissue loss to receive the 30 minute massage. In another embodiment the massage therapy is provided on a weekly basis in conjunction with weekly body composition testing. This provides the participant with additional accountability and stress management although typically at a greater monetary cost to the participant. As is evident to one of ordinary skill in the art, the program can be modified in length and in the frequency of testing without departing from the spirit of the invention.

The reward and behavior modification formula does have exceptions. First, the formula is modified for individuals with eating disorders or medical conditions that make the goal structure undesirable. These exceptions are at the discretion of the Registered Dietitian. For example, if the individual has an eating disorder that tempts them to purge prior to the body composition testing then the reward structure should be changed. One way to change the goal is to base the goal on healthy eating. The RD can set a specific nutritional goal every 2 weeks such as, eating 25 g of fiber every day. The client submits a food journal to the RD for review during each of the body composition tests. If the individual met his or her nutritional goal, then he or she receives the massage or reward.

Another exception to the general formula occurs when a male achieves 15% body fat, or when a female achieves 25% body fat. These percentages of body fat are extremely healthy, therefore, it is not necessarily in the best interest of these participants to continue to lose fatty tissue. Therefore, once a participant reaches this level of body fat, they automatically receive their reward massages as long as they maintain their desired body fat percentage. In this way, the system rewards the individuals for maintaining a healthy body composition.

Some individuals are not interested in losing weight, but rather desire to gain weight. This leads to another exception to the general rule. For the individuals whose goal is to gain weight, they can also earn the massage reward based upon their performance within the program. The weight gain formula requires the individual's fatty tissue pounds to stay the same or decrease while their lean body mass percentage increases. If the participant's weight gain is coming from fatty tissue, then the participant does not receive a massage or reward. The system does not quantify how much lean mass the individual must gain for each body composition test because each person's body builds muscle at different rates.

The preferred embodiment utilizes massage therapy as a reward for achieving weight management goals, as a tool for behavior modification and stress management. The inventor has discovered that utilizing massage therapy according to the preferred embodiment has resulted in dramatically improved results over providing the components of the invention as individual services without the invention's accountability and reward structure.

Not only does the massage therapy act as a reward for healthy weight loss, but the massage therapy also acts as a stress management tool helping the individual cope with the stress accompanying the dietary changes implemented within the system. The system helps the individual replace old habits with a new healthier habit. For example, if the individual's coping mechanism for stress is to overeat, the system helps the individual change that coping mechanism to massage therapy over time. Teaching the individual that they are sabotaging their reward of a massage by overeating or unhealthy eating, the individual learns to not turn to food for stress management but rather, to refrain from overeating and rely on the massage therapy for stress management.

Although this system has shown significant success using massage therapy as both a positive reinforcement tool and a stress management tool within the system, other rewards or stress management tools could be utilized. For example, some may not be motivated by massage therapy or in some cases may be medically discouraged from massage therapy. In these cases alternative rewards and stress management tools may be utilized to motivate the individual while promoting healthy weight management.

This program does not require a specific fitness program. The system is effective as a "calories in" system. However, a fitness or exercise program may be incorporated into the system. One of ordinary skill in the art will recognize that all types of exercise and fitness can be incorporated into the program while complimenting the overall system.

Other alterations, variations and combinations are possible that fall within the scope of the present invention. Although the preferred embodiments of the present invention have been described, those skilled in the art will recognize other modifications that may be made that would nonetheless fall within the scope of the present invention. Therefore, the present invention should not be limited to the apparatus and method described. Instead, the scope of the present invention should be consistent with the invention claimed below.

I claim:

1. A method for reducing an individual's fatty tissue mass relative to the individual's lean body mass comprising:
   a) testing a first body composition of the individual with a fat/lean analysis device having a margin of error less than or equal to 2%, and setting a target fat/lean mass for the individual based upon the first body composition;
   b) testing a metabolic rate of the individual and setting a caloric intake range for the individual based upon the metabolic rate;
   c) providing counseling to the individual by a nutritional counselor;
   d) testing a second body composition of the individual with the fat/lean analysis device after the testing the first body composition step,
   providing the individual with massage therapy if the individual achieves the target fat/lean mass, and adjusting the target fat/lean mass for the individual based upon the second body composition,
   retesting the metabolic rate of the individual if the individual's caloric intake was within caloric intake range and the individual did not achieve the target/lean mass, and resetting the caloric intake range for the individual based upon the retested metabolic rate of the individual;
   e) testing a third body composition of the individual with the fat/lean analysis device after the testing the second body composition step,
   providing the individual with massage therapy if the individual achieves the target fat/lean mass, and adjusting the target fat/lean mass for the individual based upon the third body composition,
   retesting the metabolic rate of the individual if the individual's caloric intake was within caloric intake range and the individual did not achieve the target/lean mass, and resetting the caloric intake range for the individual based upon the retested metabolic rate of the individual;
   d) testing a fourth body composition of the individual with the fat/lean analysis device two weeks after the testing the third body composition step,
   providing the individual with massage therapy if the individual achieves the target fat/lean mass, and adjusting the target fat/lean mass for the individual based upon the fourth body composition,
   retesting the metabolic rate of the individual if the individual's caloric intake was within caloric intake range and the individual did not achieve the target/lean mass, and resetting the caloric intake range for the individual based upon the retested metabolic rate of the individual;
   wherein the individual's body composition is retested biweekly for at least 12 weeks.

2. The method of claim 1 wherein the fat/lean analysis device is a plethysmographic air chamber, a magnetic resonance imaging scanner, or a computed tomography scanner.

3. A method for managing an individual's fatty tissue mass relative to the individual's lean mass comprising:
   a) testing a body composition of the individual with an analysis device having a margin of error less than or equal to 2% in testing the individual's fatty tissue mass and lean mass, and setting a target fat/lean mass for the individual based upon the first body composition, wherein the body composition of the individual includes the individual's fatty tissue mass and the individual's lean mass; and setting a target fatty mass for the individual based upon the body composition of the individual;
   b) testing a metabolic rate of the individual and setting a caloric intake range for the individual based upon the metabolic rate;
   c) providing counseling to the individual by a registered dietitian;
   d) retesting the body composition of the individual biweekly with the analysis device, wherein after each retest
   providing a massage therapy to the individual if the target fatty mass is achieved, and resetting the target fatty mass for the individual based upon the retested body composition of the individual;
   retesting the individual's metabolic rate if the individual's caloric intake was within caloric intake range and the individual did not achieve the target fatty mass, and resetting the caloric intake range for the individual based upon the retested metabolic rate of the individual.

4. The method of claim 3 further comprising questioning the individual with a questionnaire, the questionnaire questioning the individual's gender, height, weight, current exercise habits, weight management goals, weight management history, factors motivating the individual, daily activity levels, body type, health, and medical conditions.

5. The method of claim 3 wherein testing the metabolic rate of the individual further comprises measuring the oxygen consumption of the individual.

6. The method of claim 3 further comprising biweekly retesting of the body composition of the individual for at least twenty six weeks.

7. The method of claim 3 further comprising re-counseling the individual by the registered dietitian.

8. The method of claim 2 wherein the testing of the metabolic rate of the individual includes measuring the oxygen consumption of the individual.

9. A lifestyle management method for motivating an individual to achieve a measured one pound bi-weekly body fat reduction goal while maintaining lean mass, the lifestyle management method comprising the steps of:
   a) measuring a first body fat weight in the individual with an analysis device selected from a group consisting a plethysmographic air chamber, a magnetic resonance imaging scanner, and a computed tomography scanner;
   measuring a first body lean weight in the individual with the analysis device;
   measuring a first metabolic rate for the individual and setting a caloric intake range for the individual based upon the metabolic rate;
   b) measuring a second body fat weight of the individual with the analysis device two weeks after the first body fat weight measurement to determine a bi-weekly body fat change;
   measuring a second body lean weight of the individual with the analysis device two weeks after the first body lean measurement to determine a bi-weekly body lean change;
   providing a massage therapy to the individual if the bi-weekly fat change is greater than one pound;
   measuring a second metabolic rate for the individual and resetting the caloric intake range if the biweekly fat change is less than one pound and the individual's caloric intake between the measurements of the first body fat weight and the second body fat weight was within the caloric intake range;

c) every two weeks for at least an additional four (4) weeks measuring a recent bi-weekly body fat change and a recent bi-weekly body lean change of the individual with analysis device
d) encouraging the individual with massage therapy when the recent bi-weekly body fat change achieves the measured one pound bi-weekly body fat reduction goal; and
e) measuring a recent metabolic rate for the individual and resetting the caloric intake range if the recent bi-weekly fat change is less than one pound and the individual's caloric intake between was within the caloric intake range.

10. The lifestyle management method of claim 9 further comprising the step of:
f) providing the individual with a first Registered Dietician consultation to aide the individual in achieving the one pound body fat reduction reward threshold.

11. The lifestyle management method of claim 10 further comprising of step of:
g) measuring a second metabolic rate; and
h) providing the individual with a second Registered Dietician consultation when the caloric intake range is reset.

12. The lifestyle management method of claim 11 wherein the first and second measuring of the metabolic rate is indirect calorimetry.

13. The method of claim 3 further comprising the steps of:
d) bi-weekly retesting of the body composition of the individual for twenty six weeks; and
e) providing the individual with an additional massage therapy when a recent body composition test indicates a bi-weekly one pound body fat reduction.

14. The method of claim 1 wherein the target fat/lean mass includes a one pound reduction in fatty tissue mass.

15. The method of claim 1 wherein the target fat/lean mass includes a one pound reduction in fatty tissue mass
if the individual is male and the fatty tissue mass exceeds more then 15% of the individual's combined lean tissue mass and fatty tissue mass, or
if the individual is female and the fatty tissue mass exceeds more then 25% of the individual's combined lean tissue mass and fatty tissue mass.

16. The method of claim 1 wherein the individual's body composition is retested biweekly for at least 26 weeks.

17. The method of claim 3 wherein the analysis device is selected from a group consisting a plethysmographic air chamber, a magnetic resonance imaging scanner, or computed tomography scanner.

* * * * *